United States Patent [19]

Vince

[11] Patent Number: 4,594,350

[45] Date of Patent: Jun. 10, 1986

[54] (3-ETHOXYPROPIONATE) ESTERS OF CYCLARADINE

[75] Inventor: Robert Vince, St. Paul, Minn.

[73] Assignee: Reagents of University of Minnesota, Minneapolis, Minn.

[21] Appl. No.: 635,389

[22] Filed: Jul. 30, 1984

[51] Int. Cl.[4] .................. C07D 473/00; A61K 31/52
[52] U.S. Cl. .................................. 514/261; 544/277
[58] Field of Search .................. 424/253; 544/277; 514/261

[56] References Cited

U.S. PATENT DOCUMENTS

| 4,138,562 | 2/1979 | Vince | 544/326 |
| 4,268,672 | 5/1981 | Vince | 544/265 |
| 4,362,729 | 12/1982 | Vince | 424/253 |
| 4,383,114 | 5/1983 | Vince | 544/277 |

FOREIGN PATENT DOCUMENTS 42596  3/1984  European Pat. Off. .

OTHER PUBLICATIONS

Dorland's Illustrated Medical Dictionary, W. B. Saunder's, 26th edition, 1981, p. 1388.
Science, vol. 220, pp. 292-293, (Apr. 15, 1983).
Abstracts of Papers, 185th ACS National Meeting, Seattle Washington, Mar. 20-25, 1983, Carbohydrate Chem. Abstracts Nos. 24-46.
The New England Journal of Medicine, vol. 310, (No. 24), pp. 1545-1550, (Jun. 14, 1984); S. E. Straus et al.
The New England Journal of Medicine, vol. 310, (No. 24), pp. 1551-1556, (Jun. 14, 1984); J. M. Douglas et al.
Annals of Internal Medicine (1984), vol. 100, pp. 823-828; J. C. Wade et al.
Annals of Internal Medicine (1984), vol. 100, pp. 920-921; R. Ambinder et al.
Vince, R. et al., *J. Med Chem.*, (1977) 20: pp. 612-613; Carbocyclic Arabinosyladenine, an Adenosine Deaminase Resistant Antiviviral Agent.
Shannon, W. et al., *Antimicrob. Agents and Chemother.*, (1983), 24, pp. 538-543; Comparison of the Efficacy of Vidarabine, its carbocyclic Analog (Cycladarine), and Cylaradine-5'-Methoxyacetate in the Treatment of Herpes.
Vince, R. et al., *Science*, (1981), 221, pp. 1405-1406; Carbocyclic Arabinofuranosyladenine(Cycladarine); Efficacy against Genital Herpes.

*Primary Examiner*—Ethel G. Love
*Attorney, Agent, or Firm*—Thomas Hoffman; Gerald S. Rosen

[57] ABSTRACT

Antiviral (3-ethoxypropionate) esters of (+)-cycladarine having the formula:

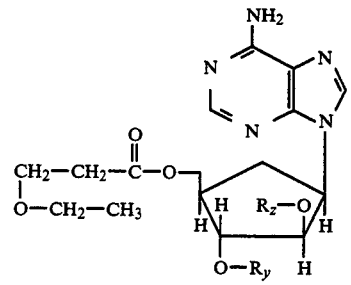

In the monoester Ry and Rz are hydrogen. In the diester Ry is the 3-ethoxypropionyl group and Rz is hydrogen. In the triester, Ry and Rz are each 3-ethoxypropionyl groups.

20 Claims, No Drawings

(3-ETHOXYPROPIONATE) ESTERS OF CYCLARADINE

BACKGROUND OF THE INVENTION

1. Field of the Invention

The invention is directed to the 3-ethoxypropionate esters of cyclaradine useful in the treatment of certain viral infections. Additionally, the invention involves orally, parenertally and topically acceptable formulations of the esters and method of utilizing same to treat susceptible viral infections.

2. Description of the Prior Art

U.S. Pat. No. 4,362,729 (R. Vince) discloses ($C_1$–$C_6$)alkoxy($C_1$–$C_6$)alkanoyl esters of ($\pm$)-cyclaradine and topically acceptable antiviral formulations useful for treating susceptible viral infections. Only the methoxyacetate ester is specifically disclosed.

U.S. Pat. No. 4,138,562, issued Feb. 6, 1979, and J. Med. Chem., 20, 612, (1977) discloses the synthesis of the nucleoside($\pm$)-9-[$2\alpha,3\beta$-dihydroxy-$4\alpha$-(hydroxymethyl)cyclopent-$1\alpha$-yl]adenine which will hereinafter be referred to more simply as ($\pm$)cyclaradine. ($\pm$)-Cyclaradine is the parent racemic alcohol of the 3-ethoxypropionate ester of this invention. The parent racemic alcohol and the simple alkanoate esters thereof are the subject of U.S. Pat. No. 4,268,672, issued May 19, 1981.

Cyclaradine, in its racemic and optically active forms, exhibits potent antiviral activity, in vitro, against viral pathogens such as Herpes and is resistant to the enzyme adenosine deaminase (a normal constituent of human serum) which is responsible for the destruction of the antiviral properties of currently available antiviral nucleosides such as 9-$\beta$-D-arabinofuranosyladenine. It has subsequently been found, however, that cyclaradine and its simple alkyl esters are significantly more active in vivo than expected. Moreover, U.S. Pat. No. 4,302,729 discloses that the alkoxyalkanoate esters, and specifically the methoxyacetate ester are only active topically.

SUMMARY OF THE INVENTION

This invention provides the racemic, ($\pm$), and optically active, (+), forms of (3-ethoxypropionate)esters of cyclaradine which exhibit surprisingly greater in vivo oral activity than the parent alcohols or its simple alkanoate esters, or the mono, di or tri(methoxyacetate)esters. The compounds of this invention are represented by the formula:

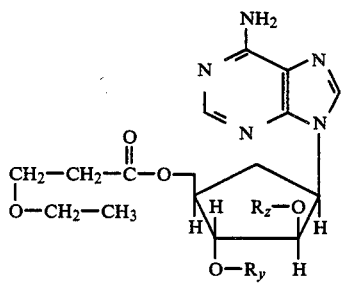

wherein:
in the monoester: Ry and Rz are hydrogen
in the diester: Ry is

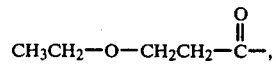

Rz is hydrogen, or
in the triester: Ry and Rz are

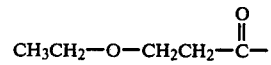

The racemic and optically active monoesters of cyclaradine are preferred. A particularly preferred embodiment is the optically active (+) form wherein Ry and Rz are hydrogen, i.e., (+)-Cyclaradine, 5'-(3-ethoxypropionate).

In addition to significantly increased in vivo oral activity, the novel 3-ethoxypropionate esters also possess the advantage of increased water solubility which greatly facilitates the preparation of aqueous dosage forms, e.g., cream and other aqueous formulations desirable for topical, oral and parental administration. The increased water solubility cannot itself explain the enhanced in vivo oral effectiveness of the compounds of this invention since the simple hydrochloride salt of cyclaradine is highly water soluble, and have the same activity when applied to the skin as the claimed compounds, or even cyclaradine itself but is not orally active. However, the 3-ethoxypropionate esters of this invention are orally active.

PREPARATION OF CYCLARADINE

The accompanying figure is a flow diagram showing the preparation of (+)-cyclaradine useful for preparation of the 5'-(3-ethoxypropionate)esters of (+)-cyclaradine of the present invention.

DESCRIPTION OF THE PREFERRED EMBODIMENTS

The preferred antiviral compound 9-[$2\alpha,3\beta$-dihydroxy-$4\alpha$-(3-ethoxypropoxymethyl)cyclopent-$1\alpha$-yl]adenine ester (formula 2 wherein Ry and Rz are hydrogen) is prepared by reaction of (+)-(or($\pm$)-cyclaradine with from about one equivalent of an 3-ethoxypropionyl halide, $C_2H_5OCH_2CH_2COX$ wherein X is halogen, e.g., fluoride or chloride. The anhydride of 3-ethoxypropionic acid may be used in place of its acid halide. About one equivalent of 3-ethoxypropionyl halide, e.g., chloride, is added to a solution of ($\pm$) or (+)-cyclaradine (or an acid salt, such as hydrochloride, thereof) in a non-polar, non-reactive, water-miscible solvent, such as dimethylformamide (DMF), dimethylacetamide, tetrahydrofuran (THF), pyridine, or the like. The reaction is carried out at about 4° C. for about 12 to 18 hours with stirring. Water is added to quench the reaction. Volatiles are removed and the ester product is recovered and purified. The monoester results from the reaction of one equivalent of the 3-ethoxypropionic acid halide, the diester from two equivalents, etc.

As used herein, "pharmaceutically acceptable salts" means acid addition salts formed from mineral acids such as hydrochloric, hydrobromic, phosphoric or sulfuric acids or formed from organic carboxylic or sulfonic acids such as trifluoroacetic, para-toluene sulfonic, maleic, acetic, citric, oxalic, succinic, benzoic, tartaric, fumaric, mandelic, ascorbic or malic acids.

The figure schematically illustrates the conversion of (−)-aristeromycin into (+)-cyclaradine (Compound 1). Since the conversion of compound 6 into compound 7 depicted in the Figure gave high net inversion of configuration, the absolute configuration of (+)-cyclaradine is known. The conversion of compound 1 into the 5′-(3-ethoxyproprionate)monoester of compound 2 is effected under conditions that in similar systems gave high net retention of configuration. Thus, the absolute configuration of the monoester (Ry and Rz are hydrogen, and of the diester (Ry is 3-ethoxyproprionate and Rz is hydrogen) and of the triester (Ry and Rz are 3-ethoxyproprionate) are as shown hereinabove.

The invention is illustrated by the following examples:

EXAMPLE 1

Preparation of the 1,3-Dichloro-1,1,3,3-tetraisopropyldisiloxane of (−)-Aristeromycin (Compound 4)

To a solution of isopropylmagnesium bromide, in a 2 L round bottom flask equipped with stirrer, a reflux-condenser and dropping funnel, prepared by adding magnesium (19.5 g 0.8 mole) and isopropyl bromide (78 mL, 0.8 mole) in diethyl ether (250 mL) under a dry nitrogen atmosphere, trichlorosilane (28 mL, 0.28 mole) in diethyl ether (50 mL) was added slowly. The reaction mixture was refluxed for 6 hrs. and 300 mL of 10% hydrochloric acid was slowly added. The ether layer was separated and the aqueous layer was extracted with ether (3×200 mL). The combined organic layers were washed with water, dried and concentrated to 23.7 g (0.1 mole 71% yield) of 1,1,3,3-tetraisopropyldisiloxane as an oil. I.R., neat, $\nu$ for Si—H=2110 cm$^{-1}$; mass spectra: M+=246 amu, M-(i-pr)=203 amu.

A carbon tetrachloride solution saturated with chlorine at room temperature was added into magnetically stirred 1,1,3,3-tetra-isopropylsiloxane (12.3 g, 0.05 mole) under exclusion of moisture until reaction mixture stayed yellow. The reaction can be followed by the disappearance of I.R. Si—H band at 2100 cm$^{-1}$. The reaction mixture was concentrated and distilled under reduced pressure to give the title compound (4.2 g, 0.045 mole, 90% of theory) as colorless liquid; bp 120°/15 mm; mass spectrum: M+-(i-pr)=271 amu.

EXAMPLE 2

Preparation of 3′,5′-Tetraisopropyldisiloxane-1″,3″-diylaristeromycin (Compound 5)

3.0 g (0.0113 mole) of (−)-aristeromycin (Compound 3) was dissolved in 700 mL of anhydrous pyridine. With stirring under a dry atmosphere, 3.56 g (0.0113 mole) of 1,3-dichloro-1,1,3,3-tetraisopropyldisiloxane, the title compound of Example 1, was added. The reaction mixture was allowed to stir for 18 hours at room temperature. Excess water was added and the reaction mixture so formed was concentrated to a gum. The crude product was redissolved in 100 mL of dichloromethane and the resulting solution was washed with 3×25 mL of water. The organic layer was evaporated under reduced pressure to a gum, chromatographed on a 2.5×60 cm silica gel column using 2% (v/v) methanol in chloroform as eluant to give 4.2 g of the title compound, 74% yield.

EXAMPLE 3

Preparation of 2′-O-Trifyl-3′,5′-tetraisopropyldisiloxane-1″,3″-diylaristeromycin (Compound 6)

125 mg (0.25 mmole) of the title compound of Example 2 and 95 mg (0.78 mmole) of 4-dimethylaminopyridine were dissolved in 10 mL of dichloromethane at −78° under a dry argon atmosphere. Trifluoromethylsulphonyl chloride 75 μL (0.7 mmole) was added in one portion. The reaction mixture was stirred at −78° C. for 5 minutes, allowed to warm to room temperature gradually over 0.5 hrs. The mixture was diluted with ethyl acetate (25 mL) and washed with (3×5 mL) dilute hydrochloric acid, (1×5 mL) water followed by (1×5 mL) saturated sodium bicarbonate and (1×5 ml) water. The organic layer was dried over magnesium sulfate and evaporated to dryness leaving 160 mg of the title compound, a solid.

EXAMPLE 4

Preparation of 2′-O-Acetyl-3′,5′-tetraisopropyldisoloxane-1,3-diyl(+-)cyclaradine (Compound 7)

160 mg of the title compound of Example 3 was dissolved in 2 mL of hexamethylphosphoramide containing 300 mg of tetraethylammonium acetate. The reaction mixture was allowed to stir for 1 hour under an argon atmosphere. The mixture was poured in to 50 mL of ethyl acetate, washed sequentially with saturated sodium chloride solution, dilute hydrochloric acid, water (twice), saturated sodium bicarbonate solution and finally with saturated sodium chloride solution. The organic layer was dried over magnesium sulfate and concentrated under reduced pressure to give the title compound.

EXAMPLE 5

Preparation of (+)-cyclaradine (Compound 1)

100 mg of the title compound of Example 4 was dissolved in 2 mL of 0.1M tetrabutylammonium fluoride in THF. The reaction mixture was allowed to stir for 0.5 hr. at room temperature. The reaction mixture was concentrated under reduced pressure to a crude solid. The crude product was dissolved in 10 mL of 10% sodium hydroxide in methanol and allowed to stir for 18 hours at room temperature. The crude product was chromatographed on a 2.5×30 cm silica gel column using (5/1/0.05, v/v/v) chloroform/methanol/ammonium hydroxide as eluant and the title compound, a solid was obtained; $[\alpha]_D^{25} = +60.1°$ (C,2, DMF).

EXAMPLE 6

Preparation of (+)-5′-(3-ethoxypropionyl)cyclaradine

Dissolve 2.0 g (7.55 mmole) of the title compound of Example 5 in 7.55 mL of 1N HCl and concentrate the solution to a residue. To the stirred solution of the residue in 50 mL of DMF, add a solution of 1.2 mL of 3-ethoxypropionyl chloride dissolved in 9.5 mL of DMF. Stir the mixture for 18 hours at 3°-5° C. Add 3 mL of ice-water and thereafter, 1.5 g of NaHCO$_3$. Stir the mixture for 20 min. Remove the solid by filtration and concentrate the filtrate to a heavy oil.

Chromatograph the crude product on 100 g of silica gel eluted with (1:9, v/v)-MeOH:CHCl$_3$. Concentrate the appropriate fractions to give the title compound as a white solid. A sample of the title compound, dried in vacuum was subjected to elemental and physio-chemical analysis: Molecular weight (Fast Atom Bombardment (FAB) mass spectrometry) is 365 amu (M+); Molecular formula is $C_{16}H_{23}N_5O_5 \cdot 1.5H_2O$; mp=45°–149° C.; and $[\alpha]_D^{26}+30.8$ (C 0.5, DMF). Calculated for $C_{16}H_{23}N_5O_5 \cdot 1.5H_2O$: C,48.97; H,6.68; N,17.85; FOUND: C,49.21; H,6.11; N,16.90. The FAB mass and $^1$H-NMR are consistent with the structure assigned to the title compound of this example.

The compounds of this invention can be used in the treatment of infections caused by DNA-containing viruses such as Herpes virus, including types I and II and Herpes zoster. They can also be used in the treatment of adenoviruses, papovaviruses (warts), picodnaviruses and poxviruses.

The 5'-(3-ethoxypropionate)ester as well as the di- and triesters of (±) or (+)-cyclaradine can be formulated in standard fashion with conventionally pharmaceutical excipients for topical, oral and parenteral dosage forms.

Thus, this invention includes within its scope pharmaceutical compositions comprising the antiviral compounds of this invention in admixture with a pharmaceutically acceptable carrier therefor. In addition, the present invention also provides a method of treating or preventing susceptible viral infections in a host, e.g., animals, particularly warm-blooded animals in need of

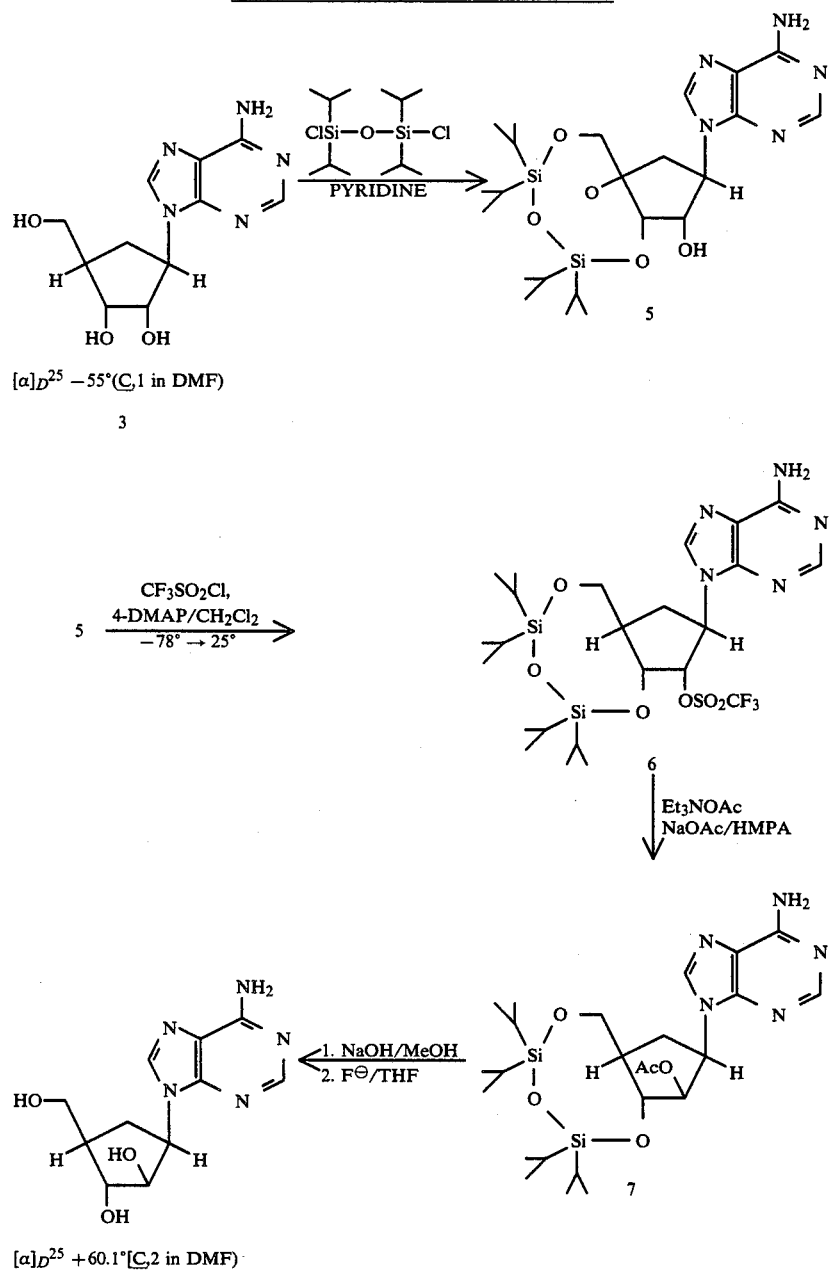

FIG. Conversion of (−)-Aristeromycin into (+)Cyclaradine such treatment or prevention, which comprises administering to said host an antiviral effective amount of a compound of this invention, or a pharmaceutical composition thereof. In the foregoing compositions, the antiviral compounds of this invention can be used as the sole active antiviral agent or in combination with other antiviral agents.

Such formulations should contain about 1–10%, preferably 1–5% and more preferably about 2.5% of weight of these esters. For oral administration, the antiviral composition of this invention may be compounded in the form of tablets, capsules, elixirs or the like. Tablet and capsules may contain such excipients as starch or lactose; liquid forms may contain coloring or flavoring agents.

Topical preparations may be in the form of creams, hydrophobic and hydrophilic ointments, or aqueous, non-aqueous or emulsion-type lotions. Typical carriers for such topical formulations are water, oil, and greases.

Injectable dosage forms, are usually liquids such as solutions or suspensions, with typical carriers being distilled water and saline solution.

For topical treatment of susceptible viral infections of the eye or genital areas, standard ophthalmic and vaginal bases, respectively, such as creams or solutions can be employed. In a typical regimen, topic formulations of this invention are applied four times daily to the affected site for a period of five to fourteen days until the infection clears. These compositions can be applied to the infected site in the usual manner. Semi-solid dosage forms can be spread manually or with an applicator, and liquid forms can be applied by dropper or spray.

The dose to be administered in any particular dosage form will depend upon various factors, such as the characteristics of the animal species being treated, the susceptibility of the infecting organism to the antibiotic, the stage and severity of the infection. Typically, the dosage administered is from about 1 mg to about 50 mg and generally about 5 mg (per kilogram of body weight) per dosage, 3–5 dosages per day, the specified dosage being determined by the judgement of the practitioner.

In treating certain patients with the compounds of this invention, it is possible to include other pharmaceutically active ingredients in the same dosage unit.

The following formulations are exemplary of the products of the invention.

TOPICAL FORMULATIONS

EXAMPLES 7–10

EXAMPLE 7

2.0% Ointment

| Ingredient | concentration (mg/g) |
| --- | --- |
| (+)-Cyclaradine, 5'-(3-Ethoxypropionate) | 20.0 |
| Propylene Glycol, USP | 100.0 |
| Propylene Glycol Stearate | 20.0 |
| White Petrolatum, USP q.s. ad to | 1.0 g |

Similarly, by increasing the amount of active ingredient to 50 mg, a 5% ointment is obtained.

EXAMPLE 8

2.5% Gel

| Ingredients | concentration (mg/g) |
| --- | --- |
| (+)-Cyclaradine, 5'-(3-Ethoxypropionate) | 25.0 |
| Poloxamer 407 | 200.0 |
| Monobasic Sodium Phosphate | 0.13 |
| Dibasic Sodium Phosphate | 0.57 |
| Water q.s. ad to | 1.0 g |

EXAMPLE 9

1.0% Cream

| Ingredients | concentration (mg/g) |
| --- | --- |
| (+)-Cylaradine,5'-(3-Ethoxypropionate) | 10.0 |
| Cetyl Alcohol | 30.0 |
| Stearyl Alcohol | 30.0 |
| Isopropyl Myristrate | 50.0 |
| Glyceryl Monostearate | 30.0 |
| Propylene Glycol | 100.0 |
| Polyoxyethylene (20 M) Monostearate | 0.5 |
| Polyoxyethylene (2 M) Monostearate | 0.3 |
| Water q.s. ad to | 1.0 g |

EXAMPLE 10

5.0% Cream

| Ingredients | concentration (mg/g) |
| --- | --- |
| (+)-Cyclaradine,5'-(3-Ethoxypropionate) | 50.0 |
| Propylene Glycol | 300.0 |
| Isopropyl Alcohol | 300.0 |
| Carbomer 940 | 15.0 |
| Sodium Hydroxide (q.s. to adjust pH) | — |
| Titanium Dioxide | 5.0 |
| Water q.s. ad to | 1.0 g |

EXAMPLE 11

5.0% Oral liquid

| Ingredients | concentration (mg/ml) |
| --- | --- |
| (+)-Cyclaradine,5'-(3-Ethoxypropionate) | 50.0 |
| Sucrose | 800.0 |
| Glycerin | 0.4 |
| Suitable color, flavor | |
| Water q.s. as to | 1 mL |

EXAMPLE 12

Capsule - Placebo

| | mg/Capsule |
| --- | --- |
| 1. Lactose USP | 106 |
| 2. Corn Starch, Food Grade | 40 |
| 3. Magnesium Stearate | 4 |
| | 150 |

EXAMPLE 13

| 2.5% Tablet | |
|---|---|
| | mg/Tablet |
| 1. (+)-Cyclaradine, 5'-3(-Ethoxypropionate) | 6.25 |
| 2. Lactose USP | 125.72 |
| 3. Corn Starch, Food Grade, as a 10% paste | 20 |
| 4. Corn Starch, Food Grade | 45 |
| 5. Magnesium Stearate | 3 |
| | 250 |

EXAMPLE 14

| 5.0% Injection Formulation | |
|---|---|
| | mg/ml |
| (+)-Cyclaradine, 5'-(3-Ethoxypropionate) | 50.0 |
| Sodium phosphate monobasic | 0.55 |
| Sodium phosphate Dibasic | 2.77 |
| Glycine | 20 |
| Purified Distilled Water q.s. ad to | 1.0 ml |

In a similar fashion, formulations for the diester and triester of (+) or (±)-Cyclaradine may be prepared.

I claim:

1. A compound represented by the formula:

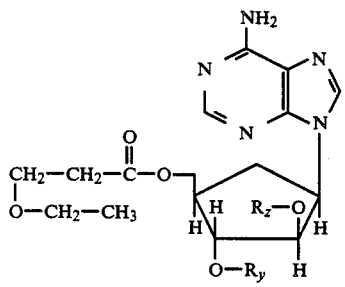

wherein $R_z$ and $R_y$ are independently hydrogen or

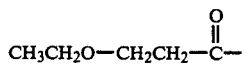

or pharmaceutically acceptable salts thereof, in racemic or optically active form.

2. The compound of claim 1 which is (+)-Cyclaradine,5'-(3-ethoxypropionate).

3. An antivirally effective pharmaceutical composition comprising an antiviral effective amount of the compound of claim 1 in admixture with a pharmaceutically acceptable carrier therefore.

4. An oral pharmaceutical composition according to claim 3.

5. A parenteral pharmaceutical composition according to claim 3.

6. A topical pharmaceutical composition according to claim 3.

7. An antivirally effective pharmaceutical composition comprising an antiviral effective amount of the compound of claim 1 in admixture with a pharmaceutically acceptable carrier therefore.

8. An oral pharmaceutical composition according to claim 7.

9. A parenteral pharmaceutical composition according to claim 7.

10. A topical pharmaceutical composition according to claim 7.

11. A method of treating susceptible viral infections, which comprises administering to a host in need of such treatment a compound of claim 1, or a pharmaceutical composition thereof, in an amount sufficient to treat such infection.

12. A method according to claim 11 wherein the route of administration is oral.

13. A method according to claim 11 wherein the route of administration is parenteral.

14. A method according to claim 11 wherein the route of administration is topical.

15. A method of treating susceptible viral infections, which comprises administering to a host in need of such treatment a compound of claim 2, or a pharmaceuticl composition thereof, in an amount sufficient to treat such infection.

16. The method according to claim 15 wherein the route of administration is oral.

17. The method according to claim 15 wherein the route of administration is parenteral.

18. The method according to claim 15 wherein the route of administration is topical.

19. The compound of claim 1 wherein $R_y$ is

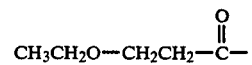

and $R_z$ is H.

20. The compound of claim 1 wherein $R_y$ and $R_z$ are

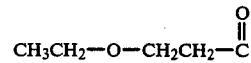

* * * * *